United States Patent [19]

Hagen et al.

[11] Patent Number: 5,340,746
[45] Date of Patent: Aug. 23, 1994

[54] COMPOSITE REACTIVE ARTICLES FOR THE DETERMINATION OF CYANIDE

[75] Inventors: Donald F. Hagen, Woodbury; Louis C. Haddad, St. Paul; Robert E. Perkins, Oakdale; Craig G. Markell, White Bear Township, Ramsey County, all of Minn.

[73] Assignee: Minnesota Mining and Manufacturing Company, St. Paul, Minn.

[21] Appl. No.: 2,198

[22] Filed: Jan. 8, 1993

[51] Int. Cl.$^5$ ............................................. G01N 33/00
[52] U.S. Cl. ................................. 436/109; 436/164; 436/169; 436/80; 422/56; 210/198.2; 210/198.3; 427/125
[58] Field of Search ............... 422/56; 436/164, 169, 436/109, 80; 210/198.2, 198.3, 502.1, 635, 656, 658; 204/129, 130; 423/42; 427/125, 214; 523/205, 137, 200, 209

[56] References Cited

U.S. PATENT DOCUMENTS

| | | | |
|---|---|---|---|
| 3,622,367 | 11/1971 | Haag et al. | 427/212 X |
| 3,635,761 | 1/1972 | Haag et al. | 427/214 X |
| 3,824,169 | 7/1974 | Van Osch et al. | 204/195 M |
| 4,153,661 | 5/1979 | Ree et al. | 264/120 |
| 4,203,952 | 5/1980 | Hancock et al. | 423/6 |
| 4,313,734 | 2/1982 | Leuvering | 23/230 |
| 4,340,473 | 7/1982 | Lindman et al. | 210/173 |
| 4,435,504 | 3/1984 | Zuk et al. | 435/7 |
| 4,460,642 | 7/1984 | Errede et al. | 428/283 |
| 4,602,987 | 7/1986 | Bonaventura et al. | 204/129 |
| 4,608,401 | 8/1986 | Martin | 523/205 |
| 4,647,477 | 3/1987 | DeLuca | 427/98 |
| 4,659,678 | 4/1987 | Forrest et al. | 436/512 |
| 4,771,086 | 9/1988 | Martin | 523/205 |
| 4,775,636 | 10/1988 | Moremans et al. | 436/518 |
| 4,810,381 | 3/1989 | Hagen et al. | 210/502.1 |
| 4,820,647 | 4/1989 | Gibbons | 436/79 |
| 4,853,335 | 8/1989 | Olsen et al. | 436/527 |
| 4,906,378 | 3/1990 | Hagen et al. | 210/635 |
| 4,952,514 | 8/1990 | Haddad | 436/80 |
| 4,971,736 | 11/1990 | Hagen et al. | 264/22 |
| 5,015,373 | 5/1991 | Carr et al. | 210/198.2 |
| 5,019,232 | 5/1991 | Wilson et al. | 204/182.8 |
| 5,058,799 | 10/1991 | Zsamboky | 228/124 |
| 5,071,610 | 12/1991 | Hagen et al. | 264/120 |
| 5,093,513 | 3/1992 | Sawicki et al. | 558/277 |
| 5,100,714 | 3/1992 | Zsamboky | 428/137 |
| 5,147,539 | 9/1992 | Hagen et al. | 210/198.3 |
| 5,147,539 | 9/1992 | Hagen et al. | 210/198.3 |
| 5,190,660 | 3/1993 | Lindoy et al. | 210/670 |

OTHER PUBLICATIONS

Hagen et al. Membrane Approach to Solid-Phase Extractions, 236 (1990), 157–164, Analytica Chimica Acta.

(List continued on next page.)

*Primary Examiner*—James C. Housel
*Assistant Examiner*—Harold Y. Pyon
*Attorney, Agent, or Firm*—Gary L. Griswold; Walter N. Kirn; Lorraine R. Sherman

[57] ABSTRACT

Composite reactive articles are useful for quantifying cyanide ions in solution. The composite reactive articles can be porous reactive supports comprising an inert substrate having immobilized thereon finely divided gold. The porous reactive supports can be particulate, porous fibrous membranes, or solution-cast membranes. Alternatively, the composite reactive articles can comprise porous fibrous membranes having enmeshed therein the aforementioned porous supports which can be in particulate or fibrous forms. The method for quantifying cyanide ions in solution comprising the steps of contacting and passing a solution containing cyanide ions through a reactive support comprising a porous, high surface area, inert substrate on which is immobilized finely divided elemental gold at a controlled rate to provide for a time to provide sufficient contact time for the gold and cyanide ions to react and provide a soluble gold cyanide complex, recovering the effluent comprising said gold cyanide complex, and determining the quantity of cyanide present in the gold cyanide complex.

10 Claims, No Drawings

OTHER PUBLICATIONS

Tanaka et al, Simultaneous Determination of Cyanide and Thiocyanate by the Pyridine/Barbituric Acid Method After Diffusion Through a Microporous Membrane, 214 (1988), 259–269, Analytica Chimica Acta.

McCarley et al, Surface Reactions of Au with Aqueous Cyanide Studied by Scanning Tunneling Micrscopy, J. Phys. Chem 1992, 96 7410–7416.

Tanaka, *Analytica Chimica acta,* 214, 259–269 (1988).

"Processing Gold Ore Using Leach-Carbon Adsorption Methods", *Information Circular, Bureau of Mines*-No. 8770, 1978.

Hagen et al., "Membrane Approach to Solid Phase Extractions", *Analytica Chimica Acta,* 236, 157–164, 1990.

Markell et al., "New Technologies in Solid Phase Extraction", LC/GC, vol. 9, No. 5, 1991.

Van Osch, et al., *Z. Anal. Chem.,* 271–4, 1975.

Romanowski, "Highly Dispersed Metals", Polish Scientific Publishers, Warsaw, Poland, pp. 52–57, 1987.

COMPOSITE REACTIVE ARTICLES FOR THE DETERMINATION OF CYANIDE

TECHNICAL FIELD

This invention relates to composite reactive articles for use in quantitating cyanide ion in solution. In another aspect, novel particulate and novel membranes comprising the novel particulate are disclosed.

BACKGROUND OF THE INVENTION

Industrial processes frequently contribute to cyanide ion contamination of ground and surface water. Such contamination is a critical problem in drinking water and cyanide ion is toxic to aquatic species in surface water. There is a great need for a more reliable and accurate method for determining levels of cyanide in environmental fluids. Classical methods usually involve acidification of an analytical sample to form HCN and distillation procedures to obtain separation. Such methods are generally unreliable due to sulfides which may be present in sample solutions and which form thiocyanate and $H_2S$ interferences in analytical determinations. Tanaka, *Analytica Chimica Acta*, 214, 259–269, 1988, described an alternate procedure using microporous permeation membranes to provide more selectivity for cyanide by flow-injection analysis. One area where cyanide is used on a large scale is in the commercial recovery of gold from low grade ores and a representative reference includes: "Processing Gold Ores using Leach-Carbon Adsorption Methods", *Information Circular, Bureau of Mines*—No. 8770, 1978.

Currently a good deal of interest has been generated in the analytical community in particle loaded membrane technology and its applications for solid phase extractions as discussed by Hagen et al. "Membrane Approach to Solid Phase Extractions" *Analytica Chimica Acta*, 236, 157–164, 1990. and by Markell et al. "New Technologies in Solid Phase Extraction" *LC/GC* Volume 9, Number 5, 1991. This technology has been shown to be useful for isolation of hydrophobic organic pollutants by adsorptive interactions and has demonstrated the advantages of fast diffusion kinetics when small, high surface area particles are packed closely together in uniform membranes with little or no channeling and controlled porosity. Van Osch et al. have described a membrane (i.e., a "pellet impervious to a solution of ions) for ion electrodes, *Z. Anal. Chem.* 271–4, 1975. These solid "membranes" disclosed in U.S. Pat. No. 3,824,169 are imporous (non-porous), chemically inert, composites of gold and salts pressed into pellets which are used in potentiometric electrode technology. These solid "membranes" should not be confused with the porous particle loaded articles disclosed in U.S. Pat. Nos. 4,153,661, 4,460,642, 4,810,381, 4,906,378, 4,971,736, 5,019,232, 5,071,610, and 5,147,539 for applications in separation science utilizing solid phase extractions.

Particle-loaded, non-woven, fibrous articles wherein the non-woven fibrous web can be compressed, fused, melt-extruded, air-laid, spunbonded, mechanically pressed, or derived from phase separation processes have been disclosed as useful in separation science. Sheet products of non-woven webs having dispersed therein sorbent particulate have been disclosed to be useful as, for example, respirators, protective garments, fluid-retaining articles, wipes for oil and/or water, and chromatographic and separation articles. Coated, inorganic oxide particles have also been enmeshed in such webs.

SUMMARY OF THE INVENTION

Briefly, the present invention discloses a method for quantifying cyanide ions in solution comprising the steps of:

a) contacting and passing a solution containing cyanide ions through a porous reactive support comprising a porous, high surface area, inert substrate on which and in which is immobilized finely divided elemental gold at a controlled rate to provide sufficient contact time to provide an effluent comprising a soluble gold cyanide complex, b) recovering the effluent comprising said gold cyanide complex, and c) determining the quantity of cyanide present in the gold cyanide complex.

In a preferred embodiment, the cyanide determining step is accomplished by:

d) analyzing for gold present in the gold cyanide complex, and e) calculating the quantity of cyanide present in the complex.

Preferably, the solution comprising cyanide ions is aqueous based (organic solvent based solutions can be used) and the inert substrate is selected from inorganic oxides or ceramics such as alumina, silica, zirconia, and porous organic polymeric substrates including carboxymethylcellulose and ion exchange resins.

In another aspect, the present invention provides novel reactive supports which can be particulate, coated particulate, coated fibers, coated fibrous membranes, or any other porous, high surface area article on the surface of which is immobilized finely divided elemental gold.

The novel reactive supports of the invention can be particulate or fibers that can be packed in a column and challenged with a cyanide ion solution to achieve the desired quantitation of cyanide ions. In other embodiments, composite reactive articles comprising porous polymeric fibrous membranes including polyamide, PTFE, porous polyolefins, cellulosics and porous solution-cast membranes (such as polyolefins) having finely divided gold immobilized thereon can be used in the method of the present invention. Many of these membranes are commercially available as filtration membranes. Porosity of the membranes before and after immobilization of finely divided gold thereon is sufficient to allow passage of fluids containing cyanide ions.

In a further aspect, the present invention provides the novel reactive supports disclosed above (in particulate or fiber form) entrapped in a porous, nonwoven fibrous web. Preferably the reactive supports (particulate or fibers) are enmeshed in a porous polytetrafluoroethylene (PTFE) fibrillated matrix. The PTFE composite matrix provides an easily handleable article for use in the method of the present invention.

Preparation of porous supports on which finely divided gold is immobilized may be provided by directly coating the support with elemental gold (e.g., by sputtering) or by coating a porous inert support with a gold salt (preferably gold chloride) solution. The coated gold salt is then reduced to elemental gold by methods well known in the art. See, for example, W. Romanowski, "Highly Dispersed Metals", John Wiley & Sons, New York (1987) 52–57.

In a preferred embodiment, a PTFE fibrillated matrix having novel reactive supports enmeshed therein is made by well-known methods. Preferably, it is made by the method disclosed in U.S. Pat. No. 5,071,610, Example 1, which is incorporated herein by reference for preparation of PTFE fibrillated matrices.

The porous supports of the invention and the composite reactive article of the invention comprising the porous supports provide a method for quantitating cyanide in solution which overcomes problems of prior art methods. In contrast to prior methods, the present invention method is not subject to numerous interferences, toxic fumes do not evolve, and the resultant analytical procedure is readily accomplished. In particular, cyanide reactions with sulfides are minimized because the gold cyanide complex ion formation of the present invention method preferably takes place at room temperature. Distillation temperatures in prior art processes promote cyanide-sulfide reactions forming isocyanates which result in a low yield of cyanide.

In this application:
"immobilized gold" means gold is tightly bound to a porous substrate so that the gold cannot be mechanically removed, e.g., by washing; the gold is finely divided and under a microscope appear as "islands" having an approximate size generally in the range of 0.1 to 100 nm, preferably 10 to 20 nm;
"void volume" means the vacancies in the structure of a composite;
"membrane" means a porous sheet material that can be fibrous or nonfibrous; preferably it has a void volume in the range 30 to 80 percent, preferably 55 to 65 percent, with a pore size of 4 to 25 nm, preferably 6 to 8 nm;
"matrix" means an open-structure entangled mass of microfibers; and
"particles" or "particulate" means porous inert substrates with solid shapes (not including PTFE) having a diameter 0.1 to 200 micrometers, preferably 5 to 40 micrometers, with an aspect ratio of 1 to 1,000,000.

As noted above, the articles can comprise porous fibrous membranes which preferably comprise a polytetrafluoroethylene (PTFE) fibril matrix having enmeshed therein reactive supports (particles), or they can comprise packed beds (columns) of the reactive supports. The articles are useful as reactive media for converting cyanide ions to soluble complex gold cyanide ions for the subsequent indirect determination of cyanide ion levels by measurement of the gold ion levels.

DETAILED DESCRIPTION OF PREFERRED EMBODIMENTS

In this invention, reactions on a solid phase are utilized to convert insoluble elemental gold in a bed of reactive supports or in a kinetically optimized composite porous membrane to a soluble gold cyanide ion species. Advantage is taken of rapid diffusion kinetics to perform fast chemical reactions, namely the reaction of cyanide with gold (zero valence state) immobilized on reactive supports or with a gold loaded membrane to generate gold cyanide ions which are soluble in water. ("Chemistry of Pseudohalides", Golub, A. M. et al., Elsevier, N.Y., pp. 97, 101, 145, 149, 155, 1986). In the method of the invention, a sample fluid is passed through a membrane or column comprising the novel reactive supports of the invention and the effluent, preferably is then analyzed for soluble gold content, and an indirect measurement of the cyanide content of the analytical sample is obtained. We have shown that cyanide in solution can be rapidly converted to a soluble gold cyanide ion using a reactive porous support or a reactive membrane composite comprising a reactive porous support which allows for the indirect measurement (calculation) of the cyanide level in liquid samples by analyzing for soluble gold concentrations in the effluent. The chemistry of gold extraction from the reactive supports of the invention can be generalized as in equations 1 and 2. A more complete description of gold-cyanide reaction mechanisms is given by McCarley etal., *J. Physical Chem.* 96, 7410–7416, 1992.

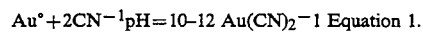

$Au^\circ + 2CN^{-1} pH = 10-12\ Au(CN)_2^{-1}$  Equation 1.

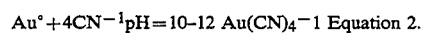

$Au^\circ + 4CN^{-1} pH = 10-12\ Au(CN)_4^{-1}$  Equation 2.

Gold can have valence states of $+1$ and $+3$. The $+1$ valence state appears to prevail in the quantifying method under conditions of room temperature and atmospheric pressure. After the solution containing CN— is passed over reactive supports of the invention, the reacted species is $Au(CN)_2^{-1}$ where the molar ratio of cyanide to gold in the ionic species is 2. With other experimental conditions, the ratio can be 4 as shown in Equation 2. Because both species of gold cyanide may be present, the analytical method must be calibrated with cyanide standards similar to the composition of the sample fluid and the conditions employed. It is important to have a sufficient amount of gold available to react with small amounts of cyanide to drive the reaction to completion for analytical recovery of cyanide. On the other hand, excessive amounts of gold should be avoided so that the method can be economically feasible. Preferably, porous reactive supports can contain the range of about 0.05 to 10% by weight of gold immobilized thereon, more preferably 1 to 6 weight percent, and most preferably 2 to 4 weight percent. This range can be extended for certain applications.

In one embodiment, the gold containing particulate is packed into beds or columns through which solutions of cyanide are passed to convert the insoluble elemental gold to the soluble gold cyanide ion species. More particularly, a high surface area particulate such as silica is coated preferably with an alcohol solution (e.g., using a combination HCl/methanol/hexane solvent) of gold chloride (preferably 1 to 10 weight percent or up to saturation), solvent is removed and gold chloride is subsequently reduced to elemental gold. The resulting reactive supports can be used in the method of the invention or the reactive supports can then be embedded in a fibrous or solution-cast membrane which preferably is a fibrillated PTFE membrane composite using the method disclosed for example, in U.S. Pat. No. 5,071,610, Example 1. In a second embodiment, a high surface area uncoated particulate (such as silica) loaded membrane is prepared according to methods disclosed in, for example, U.S. Pat. No. 5,071,610, Example 1. The enmeshed particulate in the composite membrane can subsequently be treated with a solution of a gold salt, such as gold chloride, and the gold salt which coats the surface and internal pores of the particulate is then reduced to metallic gold in-situ. In either case, it is desirable to use small (0.1 to 200 micrometer) high surface area particles which can be uniformly enmeshed in the matrix with controlled interstitial porosity.

A preferred method for preparing the PTFE composite reactive article of the invention comprises the steps of:

a) admixing lubricant (preferably water) with a blend comprising porous particulate and polytetrafluoroethylene (PTFE) particles to form a soft dough-like mass, the lubricant being present in an amount to exceed the sorptive capacity of the particulate by at least three weight percent, said mass having a cohesive consistency, and the ratio of particulate to PTFE preferably being in the range of 40:1 to 1:4;

b) intensively mixing said mass at a temperature and for a time sufficient to cause initial fibrillation of said PTFE particles;

c) biaxially calendering said mass between-gaps in calendering rolls maintained at a temperature and for a time, while closing the gap between the calendering rolls with each successive calendering operation, to cause additional fibrillation of said PTFE particles to form a self-supporting tear--resistant sheet having a void volume in the range of 30 to 80 percent and a mean pore size in the range of 0.3 to 5.0 micrometers, wherein said void volume and mean pore size vary directly with and are controlled by the amount of lubricant present during processing.

More particularly, preparation of porous fibrous and porous solution-cast membranes, for immobilization of gold thereon or for entrapment of reactive supports of the invention therein, can be as follows:

A. PTFE Membranes (Webs)

In one embodiment of the article of the present invention, an aqueous PTFE dispersion is used to produce a fibrillated web. This milky-white dispersion contains about 30% to 70% (by weight) of minute PTFE particles suspended in water. A major portion of these PTFE particles range in size from 0.05 $\mu$m to about 0.5 $\mu$m. commercially available aqueous PTFE dispersions may contain other ingredients such as surfactants and stabilizers which promote continued suspension. Examples of such commercially available dispersions include Teflon TM 30, Teflon TM 30B, and Teflon TM 42 (DuPont de Nemours Chemical Corp.; Wilmington, Del.). Teflon TM 30 and Teflon TM 30B contain about 59% to 61% (by weight) PTFE solids and about 5.5% to 6.5% (by weight, based on the weight of PTFE resin) of a non-ionic wetting agent, typically octylphenyl polyoxyethylene or nonylphenyl polyoxyethylene. Teflon TM 42 contains about 32% to 35% (by weight) PTFE solids and no wetting agent (but does contain a surface layer of organic solvent to prevent evaporation).

The composite sheet article comprising fibrillated PTFE preferably is prepared as described in any of U.S. Pat. Nos. 4,153,661, 4,460,642, and 5,071,610, the processes of which are incorporated herein by reference, by blending the desired reactive supports into the aqueous PTFE emulsion in the presence of sufficient lubricant to exceed the absorptive capacity of the solids yet maintain a putty-like consistency. This putty-like mass is then subjected to intensive mixing at a temperature preferably between 40° and 100° C. to cause initial fibrillation of the PTFE particles. The resulting putty-like mass is then repeatedly and biaxially calendered, with a progressive narrowing of the gap between the rollers (while at least maintaining the water content), until the shear causes the PTFE to fibrillate and enmesh the particulate and a layer of desired thickness is obtained. Removal of any residual surfactant or wetting agent by organic solvent extraction or by washing with water after formation of the sheet article is generally desirable. The resultant sheet is then dried. Such sheets preferably have a thickness in the range of 0.1 mm to 0.5 mm. Sheet articles with a thickness in the general range of 0.05 mm to 10 mm can be useful.

The void size and volume within such a membrane can be controlled by regulating the lubricant level during fabrication as described in U.S. Pat. No. 5,071,610. Because both the size and the volume of the voids can vary directly with the amount of lubricant present during the fibrillation process, membranes capable of entrapping particles of various sizes are possible. For instance, increasing the amount of lubricant to the point where it exceeds the lubricant sorptive capacity of the particulate by at least 3% (by weight) and up to 200% (by weight) can provide mean void sizes in the range of 0.3 $\mu$m to 5.0 $\mu$m with at least 90% of the voids having a size of less than 3.6 $\mu$m. This process can be used to create a membrane with reactive supports enmeshed therein. The PTFE which forms the web within which particulate is to be trapped can be obtained in resin emulsion form wherein the PTFE and lubricant are already pre-mixed (e.g., Teflon TM 30 or 30B, DuPont de Nemours; Wilmington, Del.). To this emulsion can be added additional lubricant in the form of water, water-based solvents such as a water-alcohol solution, or easily-removable organic solvents such as ketones, esters, and ethers, to obtain the aforementioned desired proportion of lubricant and particulate.

B. Non-PTFE Membranes (Webs)

In other embodiments of the present invention, the fibrous membrane (web) can comprise non-woven, polymeric macro- or microfibers preferably selected from the group of polymers consisting of polyamide, polyolefin, polyester, polyurethane, glass fiber, polyvinylhalide, or a combination thereof. (If a combination of polymers is used, a bicomponent fiber is obtained.) If polyvinylhalide is used, it preferably comprises fluorine of at most 75% (by weight) and more preferably of at most 65% (by weight). Addition of a surfactant to such webs may be desirable to increase the wettability of the component fibers.

1. Macrofibers

The web can comprise thermoplastic, melt-extruded, large-diameter fibers which have been mechanically-calendered, air-laid, or spunbonded. These fibers have average diameters in the general range of 50 $\mu$m to 1000 $\mu$m.

Such non-woven webs with large-diameter fibers can be prepared by a spunbond process which is well known in the art. (See, e.g., U.S. Pat. Nos. 3,338,992, 3,509,009, and 3,528,129, the fiber preparation processes of which are incorporated herein by reference.) As described in these references, a post-fiber spinning web-consolidation step (i.e., calendering) is required to produce a self-supporting web. Spunbonded webs are commercially available from, for example, AMOCO, Inc. (Napierville, Ill.).

Non-woven webs made from large-diameter staple fibers can also be formed on carding or air-laid machines (such as a Rando-Webber TM, Model 12BS made by Curlator Corp., East Rochester, N.Y.), as is well known in the art. See, e.g., U.S. Pat. Nos. 4,437,271, 4,893,439, 5,030,496, and 5,082,720, the processes of which are incorporated herein by reference.

A binder is normally used to produce self-supporting webs prepared by the air-laying and carding processes and is optional where the spunbond process is used. Such binders can take the form of resin systems which are applied after web formation or of binder fibers which are incorporated into the web during the air laying process. Examples of such resin systems include phenolic resins and polyurethanes. Examples of common binder fibers include adhesive-only type fibers such as Kodel TM 43UD (Eastman Chemical Products; Kingsport, Tenn.) and bicomponent fibers, which are available in either side-by-side form (e.g., Chisso ES Fibers, Chisso Corp., Osaka, Japan) or sheath-core form (e.g., Melty TM Fiber Type 4080, Unitika Ltd., Osaka, Japan). Application of heat and/or radiation to the web "cures" either type of binder system and consolidates the web.

Generally speaking, non-woven webs comprising macrofibers have relatively large voids. Therefore, such webs have low capture efficiency of small-diameter particulate (reactive supports) which is introduced into the web. Nevertheless, particulate can be incorporated into the non-woven webs by at least four means. First, where relatively large particulate is to be used, it can be added directly to the web, which is then calendered to actually enmesh the particulate in the web (much like the PTFE webs described previously). Second, particulate can be incorporated into the primary binder system (discussed above) which is applied to the non-woven web. Curing of this binder adhesively attaches the particulate to the web. Third, a secondary binder system can be introduced into the web. Once the particulate is added to the web, the secondary binder is cured (independent of the primary system) to adhesively incorporate the particulate into the web. Fourth, where a binder fiber has been introduced into the web during the air laying or carding process, such a fiber can be heated above its softening temperature. This adhesively captures particulate which is introduced into the web. Of these methods involving non-PTFE macrofibers, those using a binder system are generally the most effective in capturing particulate. Adhesive levels which will promote point contact adhesion are preferred.

Once the particulate (reactive supports) has been added, the loaded webs are typically further consolidated by, for example, a calendering process. This further enmeshes the particulate within the web structure.

Webs comprising larger diameter fibers (i.e., fibers which average diameters between 50 $\mu$m and 1000 $\mu$m) have relatively high flow rates because they have a relatively large mean void size.

2. Microfibers

When the fibrous web comprises non-woven microfibers, those microfibers provide thermoplastic, melt-blown polymeric materials having active particulate dispersed therein. Preferred polymeric materials include such polyolefins as polypropylene and polyethylene, preferably further comprising a surfactant, as described in, for example, U.S. Pat. No. 4,933,229, the process of which is incorporated herein by reference. Alternatively, surfactant can be applied to a blown microfibrous (BMF) web subsequent to web formation. Particulate can be incorporated into BMF webs as described in U.S. Pat. No. 3,971,373, the process of which is incorporated herein by reference.

Microfibrous webs of the present invention have average fiber diameters up to 50 $\mu$m, preferably from 2 $\mu$m to 25 $\mu$m, and most preferably from 3 $\mu$m to 10 $\mu$m. Because the void sizes in such webs range from 0.1 $\mu$m to 10 $\mu$m, preferably from 0.5 $\mu$m to 5 $\mu$m, flow through these webs is not as great as is flow through the macrofibrous webs described above.

3. Solution-cast porous membranes can be provided by methods known in the art. Such polymeric porous membranes can be, for example, polyolefin, including PTFE and polypropylene, and polyamide, polyester, and glass fibers, which porous membranes can be coated with finely divided gold by any of the methods, including sputtering and gold salt reduction, known in the art to provide porous reactive supports of the invention. Porosity of membranes before and after immobilization of gold is sufficient to allow passage of fluids containing cyanide ions.

In each of these methods, diffusion and reaction kinetics determine the rates at which insoluble, elemental gold is transformed into the soluble gold cyanide ionic species. The time for diffusion is a function of the distance an analyte must migrate before contacting a particle and is estimated by Equation 3 where $t_d$ is the diffusion time, d is the distance between particles, and D is the diffusion coefficient for the fluid involved.

$$t_d = d^2/2D \quad \text{Equation 3}$$

To optimize these criteria we investigated: (1) incorporation of metallic gold using 99.95% purity, 2–5 micrometer spherical gold particulate obtained from Johnson Matthey Co., Ward Hill, Mass., (2) sputtering gold onto high surface area metal oxide substrates such as silica, zirconia, or the gold can be sputtered onto any porous substrate such as polyamide, PTFE, polyolefin (preferably polypropylene), including porous paper or porous woven or nonwoven fibrous materials, etc. A sample of sputter coated particulate was prepared using 8–10 micrometer silica (Varian Associates, Harbor City, Calif.), and (3) coating methanolic solutions of gold chloride (Aldrich Chemical Co., Milwaukee Wis.) onto these substrates with subsequent reduction to metallic gold. This latter approach using silica or other sorptive particulate coated with gold chloride and subsequently, employing a reduction step (preferably using hydrogen gas as reducing agent) to obtain elemental gold is the preferred method for this application. The method of the invention utilizes immobilized gold containing particles within a PTFE membrane composite or particle packed columns to prevent any gold other then the soluble gold cyanide ion from appearing in the effluent liquid to be analyzed. A comparative solution of the correct pH without cyanide ion was used to establish a comparative value for the membrane or column.

All comparatives were cyanide-free.

Objects and advantages of this invention are further illustrated by the following examples, but the particular materials and amounts thereof recited in these examples, as well as other conditions, and details, should not be construed to unduly limit this invention.

EXAMPLES

Example 1

In this example, Sample 1 was prepared by dissolving 300 mg of AuCl$_3$ (Auric Chloride, Aldrich Chemical Co., Milwaukee, Wis.) in 20 ml of methanol and this solution was mixed with 10 grams of chromatographic grade 8–10 micrometer diameter silica particulate, 60 to 80 Å internal pore (Varian Associates, Harbor City, Calif.). The resultant slurry was stirred for five minutes to insure adequate coating of the silica with the AuCl$_3$ solution. The slurry was then transferred to a porcelain crucible and heated at 40°-50° C. until most of the methanol was removed by evaporation. The crucible was then heated to redness (approximately 600° C.) and allowed to cool to room temperature. The coated particulate obtained was a relatively uniformly coated, purple colored particulate containing 2% by weight gold. The purple coloration was indicative of finely divided colloidal gold. A composite membrane comprising 10% PTFE and 90% by weight of the gold coated silica was then prepared as described for sorptive particulate in U.S. Pat. No. 5,071,610.

A series of trials evaluating the reactivity of the membrane were then performed with the following general procedure. A 47 millimeter diameter disk cut from the membrane sheet was placed on a Millipore filtration apparatus (Millipore Corporation, Marlborough, Mass.) fitted with a water aspirator vacuum source. Several milliliters of methanol were pulled through the disk to condition it as described by Hagen et al. (*Analytica Chimica Acta*, 236, 1990 157-164). Twenty milliliter aliquots of water adjusted to pH 10-12 with sodium hydroxide containing no cyanide and aliquots containing 10 parts per million cyanide solution were sequentially pulled through the disk. The effluent waters were analyzed for gold by an ARL 3580 Simultaneous Sequential Inductively Coupled Plasma Atomic Emission Spectrometer (Applied Research Laboratories, Valencia, Calif.). The water containing no cyanide gave no response for gold at a lower detection limit of 0.02 micrograms gold per milliliter or less than 20 parts per billion (20 ppb Au is equivalent to 5 ppb CN— as Au(CN)$_2^{-1}$). The water sample containing 10 ppm cyanide contained 19.85 micrograms gold per milliliter (52.4% recovery) in the effluent. The theoretical value assuming the Au(CN)$_2^{-1}$ complex at the 10 parts per million level of cyanide was 37.9 micrograms gold per milliliter. A second aliquot of the cyanide solution was pulled through the same disk and analysis of the eluant showed 7.80 micrograms gold per milliliter (20.6% recovery). This trial was repeated with a second fresh disk and again the comparative trial gave less then 0.02 micrograms per milliliter. The effluent after the cyanide solutions were pulled through the second disk contained 20.78 micrograms gold per milliliter (54.8% recovery) and 14.28 micrograms gold per milliliter (37.7% recovery) for the first and second aliquots respectively. Visual inspection of the disks indicated that the membranes became lighter in color after successive exposure to aliquots of the cyanide solutions and there were several white areas suggesting depletion of gold.

These results show the usefulness of the method. Consistent partial recoveries at this level are accepted in analytical chemistry provided calibration is performed. Later examples show higher recoveries using different reduction techniques.

Example 2

In this example, Sample 2 was prepared using zirconia as the substrate for the gold coated particulate because of its greater stability in basic solutions. Silica is known to dissolve at high pH levels used in this reactive system for converting insoluble elemental gold to the soluble gold cyanide complex at pH of 10-12. Forty grams of zirconia particulate, about 8 micrometer size (prepared as disclosed in U.S. Pat. No. 5,015,373, Example 5) were placed in a 500 ml round bottom flask to which was added a solution of 1.8 grams of AuCl$_3$ in 200 ml of 0.15 M HCl in anhydrous methanol. (This corresponds to a 3% by weight loading of gold on the zirconia particulate). The flask was shaken to ensure good mixing and the methanol was then removed in a flash vacuum evaporator with constant tumbling. The resulting gold chloride coated zirconia powder was a pale orange color. The gold chloride coated zirconia powder was then treated with 70 ml of 6% sodium borohydride in water to reduce the ionic gold to elemental gold. A vigorous reaction resulted and the powder turned almost black indicating an efficient conversion of ionic gold to metallic colloidal gold. The coated particulate was allowed to settle and was washed once with 100 ml of distilled water followed by two 300 ml methanol washes and one 300 ml wash with methyl t-butyl ether. The slurry was transferred to an evaporating dish and brought to complete dryness at 40°-50° C. The resulting gold coated particulate had a light purple color. Membranes were prepared with this particulate as described in U.S. Pat. No. 5,071,610, see Example 1.

A 25 mm diameter, 0.5 mm thick disk of this membrane was placed in a holder and pretreated with 20 milliliters of methanol followed by 20 milliliters of deionized water. A 20 milliliter comparative (containing no cyanide) solution of water adjusted to pH 10 was passed through the disk as a control blank reference. Five 20 milliliter aliquots of 1 microgram per milliliter cyanide were then sequentially passed through the disk with the respective eluants being collected for gold analyses. Table 1 lists the amounts of gold found in the sequential eluants.

This trial was repeated except the pH of the solutions was adjusted to 12 and the similar results were obtained.

TABLE 1

| Sample | Micrograms/milliliter of soluble gold* |
|---|---|
| Comparative | less than 0.02 |
| Aliquot 1 | less than 0.02 |
| Aliquot 2 | 0.03 |
| Aliquot 3 | 0.03 |
| Aliquot 4 | 0.26 |
| Aliquot 5 | 0.88 |

*soluble gold was present as gold cyanide ion.

Spectrophotometric analysis of the effluent indicated that residual borohydride was still present and was difficult to wash out of the membrane. Residual reducing agent can react with gold cyanide ion to provide insoluble elemental gold. The increasing amounts of soluble gold [Au(CN)$_2$] shown in Table 1 illustrate the removal of residual reducing agent with successive aliquots or washing solutions. The data show that all residual reducing agent in the reactive supports must be removed in order to provide meaningful analytical results.

Example 3

In this example, Sample 3 was prepared by pretreating 30 grams of zirconia (same as used in Example 2) with phosphate. The zirconia was placed in a centrifuge bottle and mixed with 100 ml of 10% (w/w) phosphoric acid in water. This was centrifuged to isolate the solid particulate which was then washed with 500 ml of water followed by 200 ml of 100 grams/liter trisodium phosphate. The resulting powder was then washed twice with 500 ml of water and once with 500 ml of methanol. The excess methanol was removed and the zirconia slurry transferred to a 500 ml round bottom flask. A solution of 2.3 grams of auric chloride in 400 ml of 90% methanol in water was added to the zirconia slurry in the flask. This was thoroughly mixed and the solvent was removed by flash evaporation. Two grams of sodium borohydride was then dissolved in 100 ml of 70% methanol and immediately mixed with the dry gold coated zirconia powder. A vigorous reaction took place and the zirconia powder turned very dark. The excess liquid was removed by decanting and the product washed once with water, once with methanol and once with acetone (500 milliliters each). Excess solvent was removed by evaporation at low heat and the resulting dark purple powder contained 5% by weight elemental gold. Membranes were prepared with this particulate as described in U.S. Pat. No. 5,071,610, Example 1. This trial showed that the phosphate treated zirconia was able to adsorb higher levels of gold chloride than the bare zirconia but the borohydride reduction step required numerous washing steps to eliminate the interference described in Example 2.

Example 4

In this example, Sample 4 was prepared by placing 20 grams of silica (same as in Example 1) in a round-bottom flask and mixing with a solution of 1 gram of auric chloride in 200 ml of 0.02 M HCl in methanol. The mixture was evaporated to dryness and the resulting light orange powder was mixed with 1 gram of calcium hydroxide powder (this caused the resulting mixture to turn grayish). A portion of this powder mixture was heated in a 5% hydrogen, 95% argon atmosphere to 250° C. for twenty minutes. The resulting powder was dark purple to black in color indicating a high level of colloidal gold was deposited on the silica particulate. The second portion of Sample 4 was heated to 450° C. for 20 minutes in this hydrogen atmosphere. This resulted a pinkish colored powder. Membranes were prepared with this particulate as described in U.S. Pat. No. 5,071,610. Four 25-millimeter disks, designated Disks 1, 2, 3, 4, were cut from the membrane containing gold which had been reduced at 250° C. and evaluated for cyanide reactivity with immobilized gold as described in Example 2. Table 2 illustrates the data obtained for this hydrogen reduction experiment.

TABLE 2

| Sample | Micrograms/milliliter of soluble gold |
| --- | --- |
| Comparative | 0.08 |
| Disk 1 | 2.84 |
| Disk 2 | 2.83 |
| Disk 3 | 2.87 |
| Disk 4 | 2.72 |

These results show that the recovery of cyanide is quite uniform and while the comparative value in Table 2 is slightly higher than that observed for the comparative value in Table 1, the average recovery at the 1 microgram per milliliter (1 part per million) levels of cyanide was 74%.

Example 5

Approximately 10 grams of silica (8-10 micrometer diameter particulate, Varian Associates, Harbor City, Calif.) was placed in the lid of a plastic petri dish which was inserted into a Hummer VII Sputter Coater (made by Anatech Ltd., Alexandria, Va.). The coater was set up to coat 30 nm thickness at a rate of 4 nm/min. The coater did not have a way to measure thickness; rather, it used the current in the plasma taken by a time factor to determine thickness. After the 30 nm coating, the particulate was agitated to expose new surfaces. This process was repeated until 90 nm was added to the silica in the petri dish lid. The resulting particulate had a purple coloration typical of finely divided elemental gold.

Example 6

Commercially available porous filtration membranes (Cole-Parmer, Chicago, Ill.) were sputter-coated on the same apparatus described in Example 5, except the source of the polypropylene was Freuenberg Co. (Weinheim, Germany). In this case, only one side of the membrane was coated. These membranes were in the form of disks, 47 millimeter in diameter and had pore sizes of 0.2 micrometer. The membranes coated were nylon, polytetrafluoroethylene (PTFE), and polypropylene. The coating thickness on all the membranes was 90 nanometers. An additional PTFE membrane was coated to a gold thickness of 30 nanometers. The coated membranes had the appearance of metallic gold in color on the coated side only. This is in contrast to the purple coloration of the material prepared for Example 5 because of difference in gold particle size. Similar membranes can be prepared using any of a variety of commercially available filtration membranes composed of, for example, cellulose, nitrocellulose, cellulose acetate or nitrate, polyolefins, glass fiber or polyester.

To evaluate the porosity, the membranes were mounted in a 25 mm Millipore filtration apparatus. Using vacuum, methanol and water were pulled through the membranes, demonstrating porosity.

To evaluate the ability of the membranes to react with a cyanide solution, a piece of the gold coated polypropylene membrane, approximately 0.25 square cm, was placed in a vial with about 10 ml of a 1% aqueous cyanide solution and agitated. The gold coating disappeared after 5-10 minutes, demonstrating reactivity with cyanide.

Example 7

In this example, 50 milligrams of gold chloride was dissolved in 2 milliliters 1.5 molar hydrochloric acid in methanol. Six milliliters of isopropanol was added to this solution followed by 800 milligrams of acidic alumina (75 to 150 micrometer diameter, Bio Rad Inc., Hercules, Calif.). Sixty milliliters of hexane were then added and the slurry was mixed thoroughly. The precipitate was then separated and air dried. The dry particulate was then placed in a flask and heated to 170° C. under a stream of hydrogen gas. The purple colored particulate was then washed several times sequentially with water, methanol, and acetone. This particulate was then air dried.

Example 8

In this example 80 milligrams of gold chloride were dissolved in 2 milliliters of 1.5 molar hydrochloric acid in methanol. Six milliliters of isopropanol was added to this solution followed by 800 milligrams of 100 micrometer diameter silica particulate with 300 Angstrom internal pores (DAVISIL ™, W.A. Grace Inc., Baltimore, Md.). Sixty milliliters of hexane were then added and the mixture thoroughly mixed. The gold chloride coated particulate was then separated from the liquid phase and air dried. It was then heated to 170° C. under a stream of hydrogen which reduced the ionic gold species to elemental gold resulting in a deep purple colored particulate. This particulate was then washed several times sequentially with water, methanol, and acetone followed by air drying.

This particulate was packed into a small polypropylene column, approximately 21 mm bed height (Poly-Prep Chromatography column, Bio Rad, Hercules, Calif.) and tested for its reactivity with aqueous cyanide solutions. Table 3 shows the results obtained for a comparative solution of water and 4 aliquots of water containing 1 microgram per milliliter of cyanide, all adjusted to a pH of 10.

TABLE 3

| Sample | Micrograms/milliliter of soluble gold |
|---|---|
| Blank | less than 0.02 |
| Aliquot 1 | 3.90 |
| Aliquot 2 | 3.83 |
| Aliquot 3 | 3.92 |
| Aliquot 4 | 3.88 |

These results show that the recovery of cyanide is quite uniform with a minimal comparative recovery indicating that the gold was firmly immobilized on the silica substrate. The theoretical amount of gold in each aliquot was 3.79 micrograms and the average recovery at the 1 microgram per milliliter (1 part per million) CN—level (at 100% recovery) for the four samples passed through the column was 102%.

In summary, we have shown that cyanide ion can be rapidly converted to a soluble gold cyanide complex ion in a reactive membrane composite or a packed column configuration allowing us to indirectly measure cyanide levels in water samples by analyzing for soluble gold concentrations in the effluent.

Various modifications and alterations of this invention will become apparent to those skilled in the art without departing from the scope and spirit of this invention, and it should be understood that this invention is not to be unduly limited to the illustrative embodiments set forth herein.

We claim:

1. A method for quantifying cyanide ions in solution comprising the steps of:

a) contacting and passing a solution containing cyanide ions through a porous reactive support comprising a porous, high surface area, inert substrate on which is immobilized finely divided elemental gold at a controlled rate to provide sufficient contact time to provide an effluent comprising a soluble gold cyanide complex, b) recovering the effluent comprising said gold cyanide complex, and c) determining the quantity of cyanide present in said gold cyanide complex.

2. The method according to claim 1 wherein said determining step is accomplished by the steps of:

d) analyzing for gold present in the gold cyanide complex, and e) calculating the quantity of cyanide present-in the gold cyanide complex.

3. The method according to claim 1 wherein said reactive support is selected from the group consisting of particulate, coated particulate, coated fibers, coated fibrous membranes, and porous cast membranes having finely divided gold on their surfaces.

4. The method according to claim 1 wherein said inert substrate is selected from the group consisting of inorganic oxides, ceramics, and porous polymeric fibrous or solution-cast membranes.

5. The method according to claim 1 wherein said reactive support is enmeshed in a porous fibrous membrane.

6. The method according to claim 5 wherein said fibrous membrane is selected from the group consisting of polyamide, polyolefin, polyester, polyurethane, glass fibers, polyvinylhalide, or a combination thereof.

7. The method according to claim 1 wherein said reactive support is enmeshed in a polytetrafluoroethylene matrix.

8. The method according to claim 3 wherein said solution-cast membrane is selected from the group consisting of nylon, polytetrafluoroethylene, polypropylene, cellulose, nitrocellulose, cellulose acetate, polyolefin, glass fiber, and polyester.

9. The method according to claim 1 wherein said reactive support comprises a silica substrate.

10. The method according to claim 1 wherein said finely divided elemental gold is immobilized by sputtering.

* * * * *

UNITED STATES PATENT AND TRADEMARK OFFICE
CERTIFICATE OF CORRECTION

PATENT NO. : 5,340,746
DATED : August 23, 1994
INVENTOR(S) : Donald F. Hagen et al.

It is certified that error appears in the above-indentified patent and that said Letters Patent is hereby corrected as shown below:

Col. 3, line 33, "4 to 25 nm" should read
-- 4 to $25 \times 10^2$ nm --.

Col. 3, lines 33-34, "6 to 8 nm" should read
-- 6 to $8 \times 10^2$ nm --.

Col. 4, line 10, "equations i and 2" should read
-- equations 1 and 2 --.

Col. 4, lines 14-18, replace equations 1 and 2 with

-- Equation 1.  $Au° + 2CN^{-1} \xrightarrow{pH = 10-12} Au(CN)_2^{-1}$

Equation 2.  $Au° + 4CN^{-1} \xrightarrow{pH = 10-12} Au(CN)_4^{-1}$ --.

Col. 5, line 37, "commercially" should read
-- Commercially --.

Col. 14, line 16, "present-in" should be
-- present in --.

Signed and Sealed this

Fifth Day of September, 1995

Attest:

BRUCE LEHMAN

Attesting Officer

Commissioner of Patents and Trademarks